United States Patent
Lueckge et al.

(10) Patent No.: US 9,078,636 B2
(45) Date of Patent: Jul. 14, 2015

(54) CRYO SENSITIZING AGENTS FOR THE ENHANCEMENT OF CRYOTHERAPY

(75) Inventors: Claudia Lueckge, L'Île-Bizard (CA); Ethel Rubin, Baltimore, MD (US)

(73) Assignee: Medtronic CryoCath LP, Toronto, Ontario (CA)

( * ) Notice: Subject to any disclaimer, the term of this patent is extended or adjusted under 35 U.S.C. 154(b) by 421 days.

(21) Appl. No.: 13/555,221

(22) Filed: Jul. 23, 2012

(65) Prior Publication Data

US 2013/0197496 A1 Aug. 1, 2013

Related U.S. Application Data

(60) Provisional application No. 61/591,388, filed on Jan. 27, 2012.

(51) Int. Cl.
*A61B 18/02* (2006.01)
*A61B 18/14* (2006.01)

(52) U.S. Cl.
CPC .............. *A61B 18/02* (2013.01); *A61B 18/148* (2013.01); *A61B 2018/0293* (2013.01)

(58) Field of Classification Search
None
See application file for complete search history.

(56) References Cited

U.S. PATENT DOCUMENTS

| | | | |
|---|---|---|---|
| 6,379,349 B1* | 4/2002 | Muller et al. | 606/41 |
| 2004/0116965 A1 | 6/2004 | Falkenberg | |
| 2005/0222485 A1* | 10/2005 | Shaw et al. | 600/3 |
| 2008/0119839 A1* | 5/2008 | Vancelette | 606/23 |
| 2008/0140061 A1* | 6/2008 | Toubia et al. | 606/20 |
| 2009/0182317 A1* | 7/2009 | Bencini | 606/21 |
| 2009/0299450 A1 | 12/2009 | Johnson et al. | |
| 2010/0069900 A1 | 3/2010 | Shirley et al. | |
| 2010/0285085 A1 | 11/2010 | Stankus et al. | |
| 2011/0046724 A1 | 2/2011 | Heilmann et al. | |
| 2011/0144578 A1 | 6/2011 | Pacetti et al. | |
| 2011/0160514 A1 | 6/2011 | Long et al. | |
| 2011/0160645 A1 | 6/2011 | Sutermeister et al. | |

OTHER PUBLICATIONS

Jiang, et al., Tumor Necrosis Factor-a-Induced Accentuation in Cryoinjury: Mechanisms in vitro and in vivo, Mol Cancer Ther 2008;7 (8), Aug. 2008; pp. 2547-2548.
CIPO,PCT/CA2012/001168, Apr. 2, 2013 International Search Report, pp. 1-3.
CIPO,PCT/CA2012/001168, Apr. 2, 2013 Written Opinion, pp. 1-4.
Goel et al., "Adjuvant Approaches to Enhance Cryosurgery", J. Biomech Eng., Jul. 2009, vol. 131(7):074003.
Baust et al., "Vitamin D(3) cryosensitization increases prostate cancer susceptibility to cryoablation via mitochondrial-mediated apoptosis and necrosis", BJU Int. Mar. 2012;109(6):949-58. doi: 10.1111/j.1464-410X.2011.10408.x. Epub Aug. 26, 2011.
Ismail et al., "Inhibition of the aquaporin 3 water channel increases the sensitivity of prostate cancer cells to cryotherapy", Br J Cancer. Jun. 16, 2009;100(12):1889-95.

* cited by examiner

*Primary Examiner* — Brian T Gedeon
*Assistant Examiner* — Ankit Tejani
(74) *Attorney, Agent, or Firm* — Christopher & Weisberg, P.A.

(57) ABSTRACT

A method and device for treating tissue with temperature-sensitizing adjuvants to enhance the effects of ablation therapy. The method may comprise identifying tissue to receive ablation therapy, treating the tissue with a temperature-sensitizing agent, and activating an ablation therapy device proximate the treated tissue. The device may comprise a cryo-sensitizing adjuvant operable in association with a cryotherapy device, the cryo-sensitizing adjuvant enhancing the effectiveness of tissue destruction upon application of temperatures below 0° C.

11 Claims, 10 Drawing Sheets

CRYO SENSITIZING AGENTS FOR THE ENHANCEMENT OF CRYOTHERAPY

CROSS-REFERENCE TO RELATED APPLICATION

This application claims priority to U.S. Provisional Application Ser. No. 61/591388, filed Jan. 27, 2012, entitled CRYO SENSITIZING AGENTS TO CATHETERS FOR THE ENHANCEMENT OF CRYOTHERAPY, the entirety of which is incorporated herein by reference.

STATEMENT REGARDING FEDERALLY SPONSORED RESEARCH OR DEVELOPMENT n/a

FIELD OF THE INVENTION

The present invention relates to a method and system for enhancing the effects of cryoablation, such as increasing lesion size and reducing damage to non-target tissue.

BACKGROUND OF THE INVENTION

Ablation therapy is a technique that uses temperature extremes to destroy or alter body tissue, for example cryoablation (which uses freezing temperatures) and radiofrequency ablation ("RFA," which uses heat). Such undesirable tissue may be a tumor, cardiac tissue associated with arrhythmia, or diseased tissue. Ablation catheters are typically used to perform these techniques, and may generally include a power source, an energy and/or coolant source, and one or more ablation elements (such as a Peltier cooler, a balloon through which coolant circulates, or RF electrodes).

Even though ablation may be effective for treating some conditions, techniques such as cryoablation are not always the preferred mode of treatment for some diseases. However, adoption of ablation therapy by the medical community would be enhanced by improving the visualization of the "kill zone" (for example, the treatment region within the imaged iceball edge), increasing the size of the kill zone, and/or minimizing the incursion of collateral damage to non-target surrounding tissue. The effectiveness of ablation therapy is largely dependent on the ability of the physician to predict the critical isotherm (temperature at which complete cell destruction occurs) based on the imaging feedback (for example, of the edge of the iceball), and thus the outcome of ablation can vary greatly. Further, it can be difficult to destroy target tissue at the periphery of the treatment area (such as the iceball) while avoiding damage to non-target cells.

In an exemplary cryoablation procedure, the cryoablation elements are placed in contact with living body tissue to be ablated, and the temperature of the device at the cryoablation element is reduced to a temperature well below 0° C. After cooling of the cryoablation element begins, the temperature of the tissue in contact with the cryoablation element reaches the phase transition temperature and begins to freeze. As more heat is extracted, the temperature of the device continues to drop and the freezing interface (iceball) begins to propagate outward from the surface of the cryoablation element farther into the tissue, and this may result in a variable temperature distribution in both the frozen and unfrozen regions of the tissue.

The freezing interface continues to penetrate into the tissue until either the temperature of the cryoablation element rises (for example, when the flow of coolant within the device stops) or until the heat of the living tissue surrounding the frozen lesion reaches a steady state condition (that is, the heat becomes equal to the amount of heat removable by the cryoablation element). At this point, the frozen tissue has a temperature distribution that ranges from a low cryogenic temperature at the tissue/cryoablation element interface to the phase transition temperature on the outer edge of the frozen lesion. The temperatures in the unfrozen tissue range from the phase transition temperature at the margin of the frozen lesion to the normal body temperature. In typical cryoablation protocols, the cooling system keeps the tissue frozen for a desired period of time, and then the tissue is allowed to passively heat and thaw. Depending on the procedure, the tissue may again be frozen after thawing. The application of multiple freeze-thaw (FT) cycles has been shown to beneficially impact lesion size. However, multiple FT cycles also increases treatment time and may increase the likelihood of damaging non-target tissue.

Not only do temperature variations occur at and around the treatment site, but a variety of post-freezing effects occur in tissue that must be accounted for when optimizing the effects of cryoablation. When using a cryoablation device such as a cryoprobe at sub-zero temperatures to ablate an area of tissue, the thermal effects on each cell vary depending on its distance from the cryoprobe (closer cells experiencing lower temperatures and faster freezing rates). Complete tissue destruction may occur at temperatures below approximately −40° C., and temperatures at the edge of the iceball may be around −0.5° C. Uneven cell death rates may occur between −40° C. and −0.5° C.

Damage to cells from cryoablation may be by several mechanisms, including cellular, vascular, and immunological. At higher cooling rates near the cryoprobe, direct cell damage occurs due to the presence of ice crystals both within the cell and in the extracellular space within the tissue, up to a temperature of −0.5° C. At low cooling rates, the presence of extracellular ice causes solutes concentration outside the cell to rise, which in turn causes an osmotic imbalance of the cell membrane and dehydration of the cell. Vascular mechanisms of destruction may involve the shutdown of microvasculature after freezing and resultant ischemia, direct endothelial injury, thrombosis, free-radical formation, and inflammation. Immunological mechanisms of injury, such as when treating a tumor, may include the release of proteins into the blood stream. These proteins function as antigens, which may induce an immune reaction against the remaining tumor by stimulating immune cells to produce antibodies against tumor cells. Cryoablation may also increase the level of serum cytokines and induce maturation of dendritic cells, which then stimulate T-cells against the antigen.

Similarly, RFA destroys tissue instantaneously at temperatures greater than 60° C., with mechanisms of cell death including protein denaturation and destruction of blood vessels. Like cryoablation, the outcome of treatment is difficult to predict, which effectiveness being a function of treatment time, treatment temperature, and distance of tissue from the treatment element.

Certain chemicals have been shown to increase tissue sensitivity to temperature extremes. For example, the application of temperature-sensitizing adjuvants ("TSAs") may increase the likelihood that cells within the periphery of the iceball that would otherwise remain viable will be destroyed by ablation treatment. These adjuvants (also referred to as "agents") may include thermophysical adjuvants, chemotherapeutic adjuvants, cytokines or vascular-based adjuvants, and immunomodulators. Additionally, the application of low-current energy as an adjuvant may enhance the effects of cryoablation by increasing salt ion movement through the cell membrane, thereby increasing the salt imbalance occurring during freezing.

Sensitizing an area of target tissue before or during cryotherapy is therefore desired because an increase amount of damage may be incurred by the target tissue at higher temperatures, thus minimizing the energy requirements of the treatment device. Further, collateral damage may be mitigated. For example, cryotreatment of the heart may have unintended adverse consequences on the lungs, phrenic nerve, and other parts of the body because of the intense cold required to treat areas of the heart such as the pulmonary veins.

However, a convenient method of applying these adjuvants to target tissue in vivo is needed. For example, although adjuvants such as antifreeze proteins increase tissue sensitivity to cold, such results have been obtained after soaking excised tissue in the adjuvant, not through precise adjuvant application on living target tissue during a cryoprocedure.

SUMMARY OF THE INVENTION

The present invention advantageously provides a method, system, and device for treating tissue with temperature-sensitizing adjuvants to enhance the effects of ablation therapy. The method may comprise identifying tissue to receive ablation therapy, treating the tissue with a temperature-sensitizing agent, and activating an ablation therapy device proximate the treated tissue. The temperature-sensitizing agent may be applied to the tissue by an applicator, the applicator being at least one of: an applicator integrated with the ablation therapy device, and an applicator integrated with a second device that is not the ablation therapy device. The ablation therapy may be at least one of: cryoablation and the ablation therapy device is a cryoablation device; radiofrequency ablation and the ablation therapy device is a radiofrequency ablation device; and combination thereof. The temperature-sensitizing agent may be a temperature-sensitizing adjuvant selected from the group consisting of thermophysical adjuvants, chemotherapeutic adjuvants, vascular adjuvants, immunomodulator adjuvants, aquaporin inhibitors and combinations thereof.

The applicator may be integrated with the ablation therapy device, the applicator being at least one of an ablation element having an outer surface, the outer surface being coated with a layer of temperature-sensitizing adjuvant, a distal end of the ablation therapy device, the distal end being coated with a layer of temperature-sensitizing adjuvant, a cannula slidably disposed within a lumen of the ablation therapy device and being in fluid communication with a reservoir for containing the temperature-sensitizing adjuvant; and a spray nozzle at the distal end of the ablation therapy device and being in fluid communication with a reservoir for containing the temperature-sensitizing adjuvant. Additionally or alternatively, the applicator may be integrated with the second device, the applicator being at least one of a distal end of the second device, the distal end being coated with a layer of temperature-sensitizing adjuvant, a distal end of the second device, the distal end being in fluid communication with a reservoir for containing the temperature-sensitizing adjuvant, a hypodermic needle and syringe for containing the temperature-sensitizing adjuvant; and a spray nozzle, the nozzle being in fluid communication with a reservoir for containing the temperature-sensitizing adjuvant.

The ablation element may be an expandable element, and the distal end of the device may include a plurality of indentations each sized to contain a volume of temperature-sensitizing adjuvant. Further, the ablation element may be coated with a layer of temperature-sensitizing adjuvant further includes a layer of temperature-sensitive substrate material between the ablation element and layer of temperature-sensitizing adjuvant, the layer of substrate material readily separating from the ablation element when substrate material is within a certain temperature range. Further, the distal end of the ablation therapy device may be coated with a layer of temperature-sensitizing adjuvant further includes a layer of temperature-sensitive substrate material between the ablation therapy device and layer of temperature-sensitizing adjuvant, the layer of substrate material readily separating from the ablation therapy device when the substrate material is within a certain temperature range.

The temperature-sensitizing agent may be delivered either before or after the application of ablation therapy to the tissue. The temperature-sensitizing agent is an electrode, and the electrode may be operable to emit a low current energy of between approximately 100 millivolt (mV) to approximately 500 mV for less than 1 millisecond (ms).

In a further embodiment, the method may comprise identifying tissue to be ablated; treating the tissue with a cryo-sensitizing formulation; and activating a cryoablation device proximate the treated tissue, at least a portion of the cryoablation device being coated with a layer of the cryo-sensitizing formulation used to treat the tissue, the cryo-sensitizing formulation being selected from the group consisting of thermophysical adjuvants, chemotherapeutic adjuvants, vascular adjuvants, immunomodulator adjuvants, aquaporin inhibitors and combinations thereof.

The device may comprise a cryo-sensitizing adjuvant operable in association with a cryotherapy device, the cryo-sensitizing adjuvant enhancing the effectiveness of tissue destruction upon application of temperatures below 0° C. The cryo-sensitizing adjuvant may be applied to the tissue by an applicator, the applicator being at least one of integrated with the cryotherapy device, integrated with a second device that is not the cryotherapy device. The cryo-sensitizing adjuvant may be a cryo-sensitizing adjuvant selected from the group consisting of: thermophysical adjuvants, chemotherapeutic adjuvants, vascular adjuvants, immunomodulator adjuvants, aquaporin inhibitors and combinations thereof. Alternatively, the cryo-sensitizing adjuvant may be an electrode that emits a low current energy of between approximately 100 mV to approximately 500 mV for less than 1 ms.

The applicator is integrated with the cryotherapy device, the applicator being at least one of: a treatment element having an outer surface, the outer surface being coated with a layer of cryo-sensitizing adjuvant, a distal end of the cryotherapy device, the distal end being coated with a layer of cryo-sensitizing adjuvant, a cannula slidably disposed within the cryotherapy device and being in fluid communication with a reservoir for containing the cryo-sensitizing adjuvant; and a spray nozzle located at a distal end of the cryotherapy device and being in fluid communication with a reservoir for containing the cryo-sensitizing adjuvant. Alternatively, the applicator may be integrated with the second device, the applicator being at least one of a distal end of the second device, the distal end being coated with a layer of cryo-sensitizing adjuvant, a distal end of the second device, the distal end being in fluid communication with a reservoir for containing the cryo-sensitizing adjuvant, a hypodermic needle and syringe for containing the cryo-sensitizing adjuvant, and a spray nozzle, the nozzle being in fluid communication with a reservoir for containing the cryo-sensitizing adjuvant.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

It should be noted that the drawings are not drawn to scale.

DETAILED DESCRIPTION OF THE INVENTION

As used herein, the term "enhancing the effects of ablation" refers to augmenting the vascular, immunologic, and/or direct cellular effects of cryoinjury, increasing the accuracy in predicting lesion dimensions, increasing the likelihood that cells within a viability zone will be destroyed by the ablation therapy, and/or reducing collateral damage to non-target tissue.

As used herein, the term "ablation zone" refers to the area of tissue that is thermally affected by the ablation therapy. The ablation zone includes a "destruction zone" (area in which substantially all cells are irreversibly damaged or destroyed) and a "viability zone" (area in which fewer than substantially all cells are destroyed, with more cells remaining viable than destroyed). The ablation zone may correspond to an iceball created during cryoablation or the area of tissue thermally affected by RFA, with the destruction zone having a temperature of approximately −40° C. and below, and the viability zone having a temperature of between approximately −40° C. and approximately 0° C. Likewise, the destruction zone of an RFA zone, the zone at which tissue coagulation may occur, has a temperature of between approximately 60° C. and approximately 100° C.

As used herein, the term "distal end" refers to the distal region of an ablation device and includes one or more ablation elements (such as electrodes or balloons) and adjuvant applicator elements (such as adjuvant coatings, spray nozzles, and applicator tubes). Additionally, the term "distal end" refers to the distal region of a second device and includes adjuvant applicator elements such as hypodermic needles, swabs, adjuvant coatings, spray nozzles, and applicator tubes). The term "distalmost tip" refers to the tip of an ablation or second device (for example, a tip of a balloon catheter that extends beyond the distal end of the balloon, as shown in FIG. 10B). The distalmost tip includes a smaller area than the distal end of an ablation or second device.

Figure 1A:
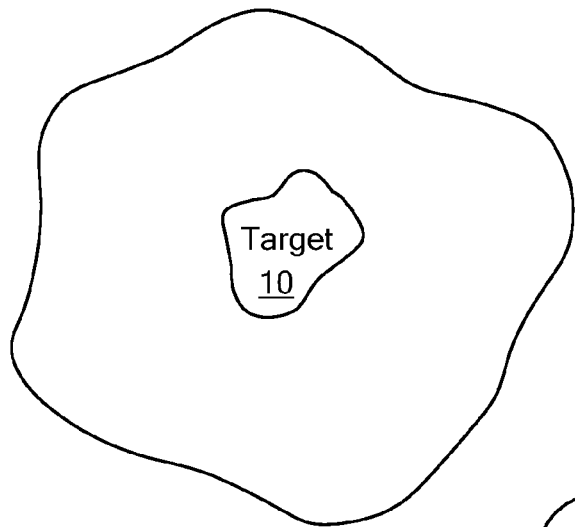
FIGS. 1A-1C show a method and exemplary results of ablating non-treated tissue, as known in the prior art.
Figure 1B:
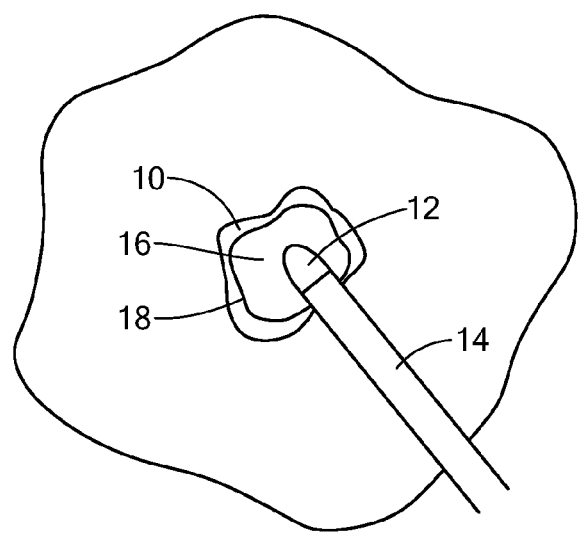
Figure 1C:
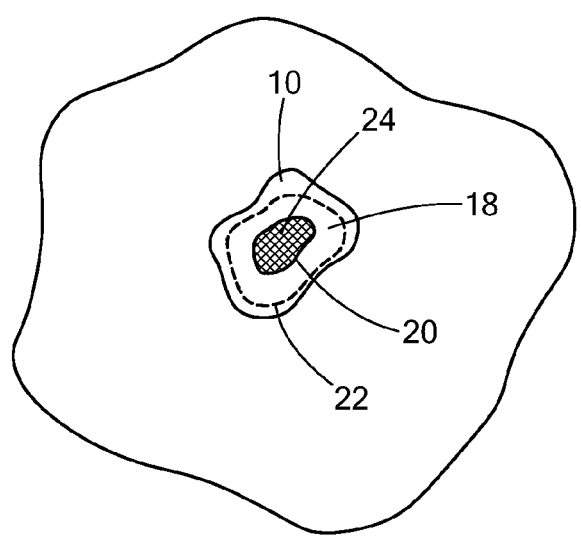

Referring now to FIGS. 1A-1C, a method and exemplary results of ablating non-treated tissue are shown, as is known in the prior art. Cryoablation is shown in FIGS. 1A-1C, with FIG. 1A depicting target tissue 10 identified for ablation (the larger outer area being non-target tissue). When the cryoablation element 12 (such as an electrode, as shown in FIG. 1A) of an ablation device 14 is placed in contact with target tissue 10 and activated, an iceball 16 forms. An iceball 16 substantially corresponds to the ablation zone 18 and includes two temperature zones: a destruction zone 20 closer to the cryoablation element (approximately -40° C. and below) and a viability zone 22 closer to the iceball 16 edge (approximately -40° C. to approximately 0° C.). Therefore, the lesion 24 (the area of tissue destroyed, corresponding to the destruction zone 20) is smaller than the ablation zone 18 (as shown in FIG. 1C, with the ablation zone 18 being depicted with dashed lines), which makes it difficult to accurately predict the size and/or shape of the lesion created. Additional FT cycles may be used to increase the size of the iceball 16, but this not only makes the procedure longer, but also increases the likelihood of damage to non-target tissue. For example, the border between target and non-target tissue may lie beneath the imaged iceball 16, making it difficult to impossible to determine whether non-target tissue is being ablated. For simplicity, the area of the ablation zone 18 and the iceball 16 area are depicted as being the same in FIG. 1B. As shown in FIG. 1B, the ablation device 14 is an ablation catheter having a fixed diameter, but could also be an ablation catheter having an expandable element such as a balloon (as shown in FIGS. 3, 4A, 4B, 10A, and 10B).

Figure 2A:
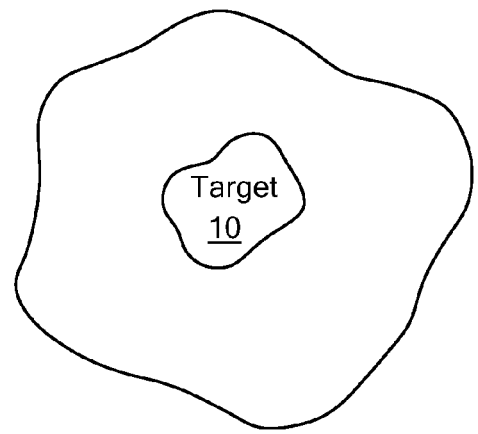
FIGS. 2A-2D show a method and exemplary results of ablating tissue treated with thermo-sensitizing adjuvant.
Figure 2B:
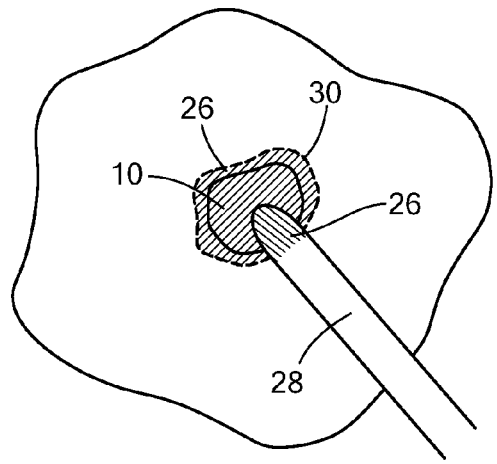
Figure 2C:
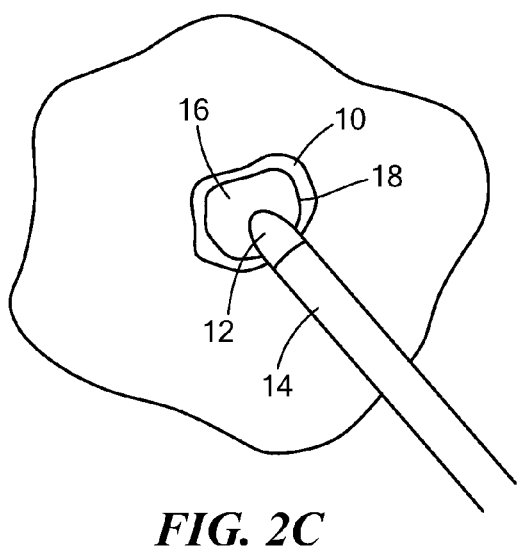

Referring now to FIGS. 2A-2D, a method and exemplary results of ablating tissue treated with thermo-sensitizing adjuvant are shown. Cryoablation is used as a non-limiting embodiment in FIGS. 2A-2D, and similar results may be effected by other ablation techniques (such as RFA). In FIG. 2A, the tissue that will receive ablation therapy ("target tissue") 10 is identified. The target tissue 10 is then treated with a temperature-sensitizing agent 26 (as shown in FIG. 2B) using an applicator 28, and the ablation therapy device 14 (such as a fixed-diameter ablation device as shown in FIG. 2C) is activated and applied to the treated target tissue 10. When cryoablation is used, an iceball 16 will form (as shown in FIG. 2C), which substantially corresponds to the ablation zone 18 and includes a destruction zone 20 and viability zone 22. For simplicity, the area of the ablation zone 18 and the iceball 16 area are depicted as being the same in FIG. 2C. The applicator 28 may be a fixed-diameter applicator, as shown in FIG. 2B; however, the applicator could be of a different type, for example, as shown and described in FIGS. 3, 4A, and 4B.

Figure 2D:
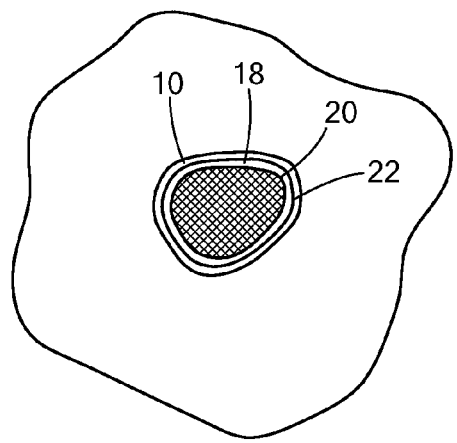

Continuing to refer to FIGS. 2A-2D, the temperature-sensitizing agent 26 may be applied both before and after ablation therapy, or temperature-sensitizing agent 26 may be applied only before or only after ablation therapy. Whether before or after ablation therapy, the temperature-sensitizing agent 26 may be applied to an area 30 that substantially corresponds to the target tissue 10, although the application area 30 may be larger than the area of target tissue 10. However, the effects of ablation therapy may only be enhanced within the ablation zone 18 (that is, tissue thermally affected by the ablation therapy). For example, the lesion may substantially correspond to the ablation zone 18, even though the application area 30 extended beyond the ablation zone 18. Further, if the TSA 26 is considered toxic to non-target tissue, the TSA 26 is carefully applied onto to target tissue 10 using the applicator 28. As shown in FIG. 2D, the lesion (depicted as the destruction zone 20) may substantially correspond to the entire ablation zone 18, effectively reducing the viability zone 22. Additionally, the depth of the destruction zone 20 may be increased, depending on the absorption characteristics of the TSA 26 and the tissue 10 to which the TSA 26 is applied.

The temperature-sensitizing agent 26 may have any of a variety of modes of action, and may be used with both cryoablation and RFA therapies. For example, the temperature-sensitizing agent 26 may be a thermophysical adjuvant, a chemotherapeutic adjuvant, a vascular adjuvant, an aquaporin inhibitor, or an immunomodulator adjuvant. However, some adjuvants may have multiple modes of action (such as TNF-a, which may be classified as both a vascular adjuvant and an immunomodulator adjuvant. Additionally, the temperature-sensitizing agent 26 may include one adjuvant, or may include a mixture of adjuvants having different modes of action. When used with cryoablation, a TSA (referred to as, in this case, a cryo-sensitizing adjuvant) may increase cell destruction within the viability zone 22 (such as at temperatures of between approximately −40° C. and approximately 0° C.), effectively increasing the destruction zone 20. The controlled application of temperature-sensitizing agents as described herein may reduce any toxic effects to non-target tissue.

Thermophysical adjuvants used as cryo-sensitizing adjuvants may include antifreeze proteins (AFPs), salts, amino acids, nucleic acids, peptides (including proteins and other polypeptides), although other thermophysical adjuvants may be used. Thermophysical cryo-sensitizing adjuvants may modify the crystalline ice phase during freezing, thereby increasing the amount of direct cell injury due to the presence of ice crystals. For example, AFPs may modify ice crystals to a spicular shape, which is effective to mechanically disrupt cell membranes and tissue connective structures. Salt solutions (such as NaCl and KCl) and amino acids (such as glycine) may induce secondary ice formation, which can enhance cell injury between −21° C. and −5° C. Additionally, thermophysical adjuvants may be effective when applied only a few minutes before cryoablation.

Chemotherapeutic adjuvants used as cryo-sensitizing adjuvants may include adriamycin, peplomycin, 5-fluorouracil, cisplatin, bleomycin, and etoposide, although other chemotherapeutic cryo-sensitizing adjuvants may be used. The use of chemotherapeutic cryo-sensitizing adjuvants with cryoablation may enhance cell destruction at temperatures between, for example, −15° C. and −5° C. Some chemotherapeutic cryo-sensitizing adjuvants may be toxic to non-target cells (such as non-tumor, normal cells), and the controlled application of these adjuvants to target tissue (such as shown and described in FIGS. 3-10) may reduce toxicity to non-target cells.

Vascular-based adjuvants used as cryo-sensitizing adjuvants may include cytokines such as TNF-a, although other vascular cryo-sensitizing adjuvants may be used. Vascular cryo-sensitizing adjuvants may increase susceptibility of the microvasculature to the vascular mode of cryoinjury. Effects may include blood coagulation, vasoconstriction, inflammation, and free-radical formation. Like chemotherapeutic cryo-sensitizing adjuvants, the controlled application of vascular cryo-sensitizing adjuvants to target tissue (such as shown and described in FIGS. 3-10) may reduce toxicity to non-target cells.

Aquaporins are, generally, small integral membrane proteins that function as molecular water channels within the cellular membrane. Aquaporin inhibitors may be used to prevent water egress from within cells during freeze duration. Such trapping of water within the cell in a localized fashion would result in greater accumulation of intracellular ice in the targeted region. Intracellular ice damages organelles and membranes, causing irreversible damage that results in cell death. A small difference in solute concentration results in a very large osmotic pressure gradient across the cell membrane; however, animal cell membranes cannot withstand any appreciable pressure gradient. Water movement may eliminate differences in osmolality across the cell membrane, but not if the water is trapped inside the cell or impeded by aquaporin inhibitors. Human hearts express mRNA for AQP-1, -3, -4, -5, -7, -9, -10, and -11, but only express AQP-1 and possible AQP-3 protein. In addition, endothelial aquaporins, which move water either into or out of the interstitial space or capillaries, depending on the direction of the osmotic gradient, would likewise be inhibited in blood vessels within the ablation target treated with aquaporin inhibiting agents. This will cause further tissue destruction from the effects of coagulation necrosis. Aquaporin inhibitors may be based on metallic (for example, mercury, silver, or gold) reactive compounds, as well as new small-molecule or peptide aquaporin blockers.

Immunomodulator adjuvants used as cryo-sensitizing adjuvants may enhance immunological cell injury by stimulating the cells of the immune system through the production of cytokines such as TNF-a and IFN-y.

Figure 3:
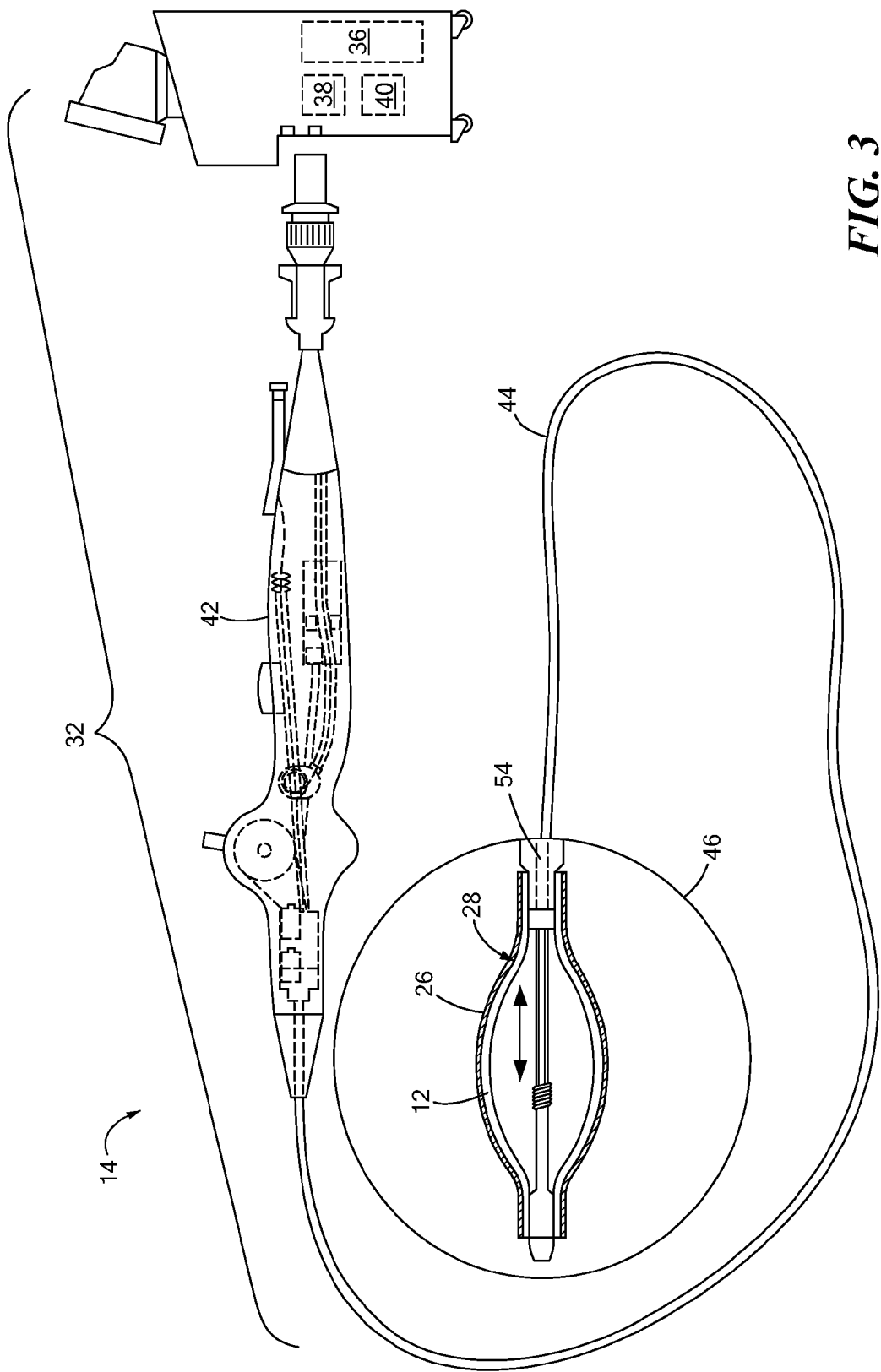
FIG. 3 shows an exemplary ablation system.

Referring now to FIG. 3, an exemplary ablation system 32 is shown. The system 32 generally includes a console 34 that houses various controls and an ablation device 14 for treating tissue. The system 32 may be adapted for cryoablation, RFA, or both. The console 34 may include one or more of a coolant reservoir 36, an RF generator 38, a TSA reservoir 40, and may further include various displays, screens, user input controls, keyboards, buttons, valves, conduits, connectors, power sources, and computers for adjusting and monitoring system parameters.

Continuing to refer to FIG. 3, the ablation device 14 may generally include a handle 42, an elongate body 44 having a distal end 46 and an ablation element 12. The handle 42 may include various knobs, levers, user control devices, input ports, outlet ports, connectors, lumens, and wires. The distal end 46 of the elongate body 44 may include one or more ablation elements 12. The one or more ablation elements 12 may be a balloon (as shown in FIG. 3), electrodes (as shown in FIG. 2C), a combination thereof, or any other type of ablation element 12. In some embodiments, the ablation element 12 may also be the TSA applicator 28, for example, a cryoablation balloon coated with a layer of TSA 26 (as shown in FIG. 3). The elongate body 44 may further include a lumen 54 in fluid communication with the coolant reservoir 36 if the device 14 is used for cryoablation. If the device 14 is used for RFA, the elongate body 44 may include a lumen 54 in communication with an RF generator 38 and/or a power source. Alternatively, the device 14 may be used for both cryoablation and RFA, in which case the device 14 may include several lumens in communication with the one or more ablation elements 12.

Referring now to FIGS. 4-12, embodiments of TSA applicators 28 are shown. Generally, the applicator 28 may be either integrated with the ablation device 14 (as shown in FIGS. 4A and 4B), or integrated with a second device 56 having a distal end 58 (as shown in FIGS. 11A), or both (as shown in FIG. 11B). Further, as shown and described in FIG. 3, for example, the ablation element 12 of the ablation device 14 may be the applicator 28 (that is, the ablation element 12 may be coated with a layer of TSA 26), or the applicator 28 may be incorporated into another area of the device 14 (for example, the distalmost tip of a balloon catheter may be coated with a layer of TSA 26, whereas the balloon is not coated). The distal end 46 of the ablation device 14 may be suited for cryoablation, RFA, or both, and may be coated with a layer of TSA 26 (as shown in FIGS. 4A, 10A, and 10B) or a substrate layer 60 and TSA layer 26 (as shown in FIG. 4B). Further, the ablation device 14 may be a fixed-diameter device (as shown in FIGS. 11A and 11B) or the ablation device 14 may have an expandable ablation element 12, such as a balloon (as shown in FIGS. 4A, 4B, 10A, and 10B). Although not shown in FIGS. 4-10, the ablation element 12 would be placed in contact with target tissue 10 during an ablation procedure, with the applicator 28 (either as part of the ablation device 14 or second device 56) being proximate or in contact with the tissue 10 to apply TSA 26.

Figure 4A:
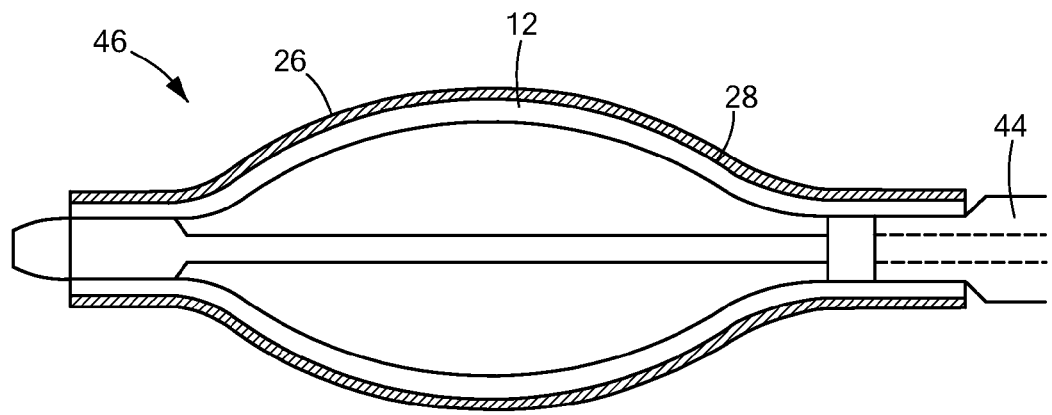
FIG. 4A shows a cross-sectional view of the distal end of a device, the device including a balloon coated with a layer of temperature-sensitizing adjuvant.
Figure 4B:
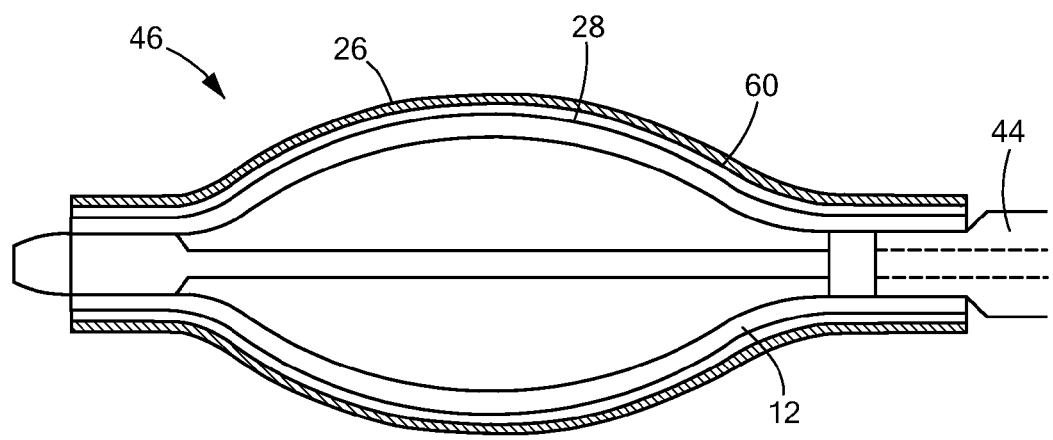
FIG. 4B shows the cross-sectional view of the distal end of a device, the device including a balloon coated with a substrate layer and layer of temperature-sensitizing adjuvant.
Figure 4C:
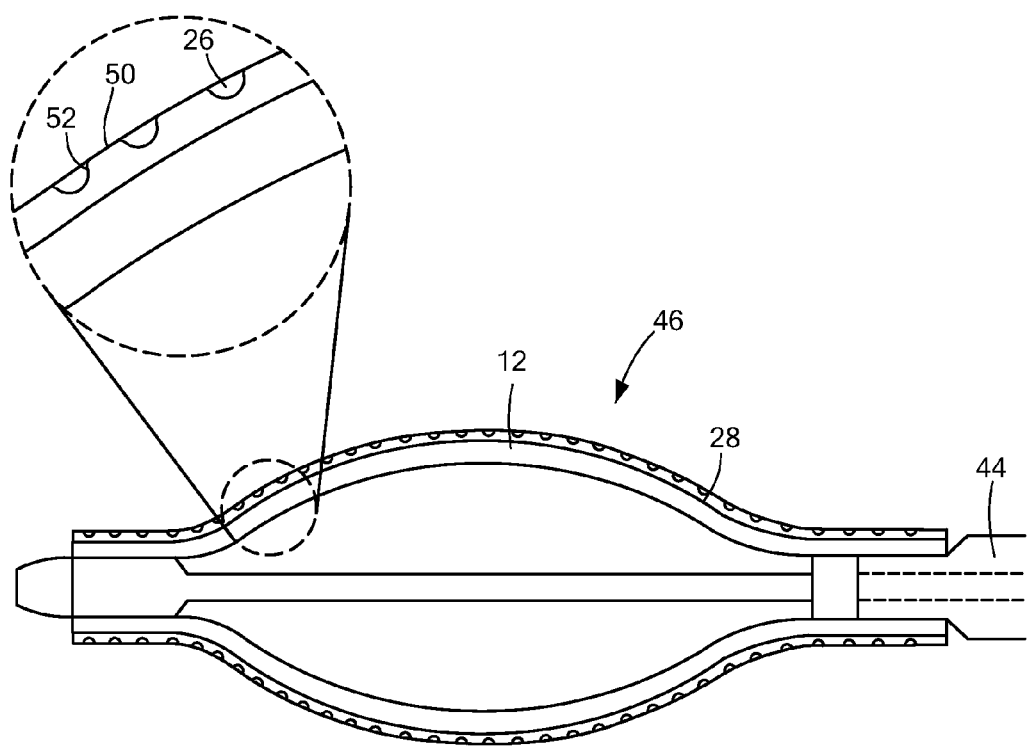
FIG. 4C shows the cross-sectional view of the distal end of a device, the device including a balloon with a layer of porous material containing temperature-sensitizing adjuvant.

Referring now to FIGS. 4A-C, cross-sectional views of the distal end 46 of an ablation device 14 are shown, the ablation device 14 including an ablation element 12 (such as a balloon, as shown in FIGS. 4A-C) coated with a layer of TSA 26. The balloon ablation element 12 may be suited for either cryoablation, RFA, or both (or neither, if the balloon functions as an applicator 28 that is part of a non-ablating second device 56), and is coated at least in part with a layer of TSA 26. Additionally or alternatively, the balloon ablation element 12 may be coated with a layer of nano- or micro-porous material 50, with small amounts of TSA 26 being contained within the nano- or micro-pores 52. When the balloon ablation element 12 is pressed against the target tissue 10, the TSA 26 may be released from the pores 52 to the tissue 10. For example, the porous material 50 may be spongelike in that it contains a plurality of throughpores. Additionally or alternatively, the porous material may contain a plurality of surface indentations (as shown in FIG. 4C). The layer of TSA 26 may be between approximately 0.01 microns to approximately 200 microns (as shown in FIG. 4A). The ablation element 12 may be additionally coated with a substrate layer 60, which may be located between the ablation element 12 and TSA layer 26 (as shown in FIG. 4B). The substrate layer 60 may include one or more temperature sensitive compounds that readily separate from the ablation element 12 when a certain threshold temperature is reached (for example, 0° C. or 60° C.). This substrate layer 60 thus facilitates movement of the TSA 26 from the distal end 46 of the ablation device 14 to the target tissue 10. Additionally or alternatively, the substrate layer 60 may be separated from the ablation element 12 by mechanical stress, for example, as when created as a balloon ablation element 12 is inflated.

Figure 5:
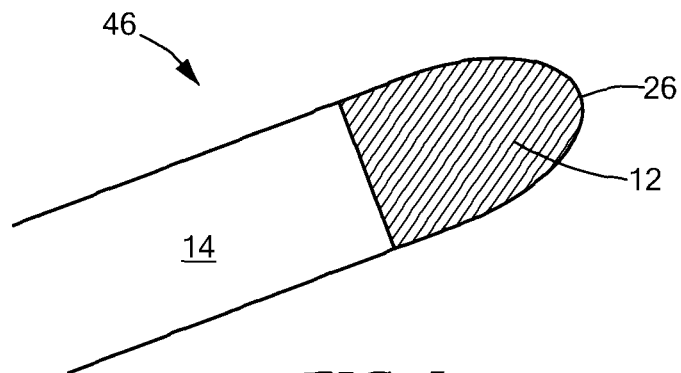
FIG. 5 shows the distal end of an ablation device, the distal tip coated with a layer of temperature-sensitizing adjuvant.
Figure 6:
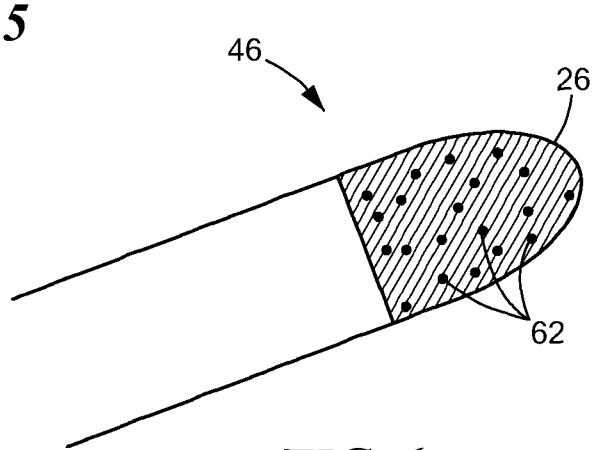
FIG. 6 shows the distal end of an ablation device, the distal tip having a plurality of depressions and being coated with a layer of temperature-sensitizing adjuvant.

Referring now to FIGS. 5 and 6, the distal end 46 of an ablation device 14 is shown, the distal end 46 being coated with a layer of TSA 26. The coated area of the distal end 56 may include an ablation element 12 (as shown in FIG. 5) suited for either cryoablation, RFA, or both (such as a focal catheter), or the coated area of the distal end 56 may not include an ablation element 12 (as shown in FIG. 6), and is coated at least in part with a layer of TSA 26. The layer of TSA 26 may be between approximately 0.01 microns to approximately 200 microns. The distal end 46 may be additionally coated with a temperature-sensitive substrate layer 60, which may be located between the distal end 46 and TSA layer 26 (as shown and described in FIG. 4B). Additionally, as shown in FIG. 6, the surface of the distal end 46 of the device 14 may include a plurality of indentations or depressions 62 sized to contain a volume of TSA 26. For example, each indentation 62 may contain as little as 0.1 µL and as much as 1 µL. The indentations 62 may either supplement or replace the TSA layer 26.

Figure 7:
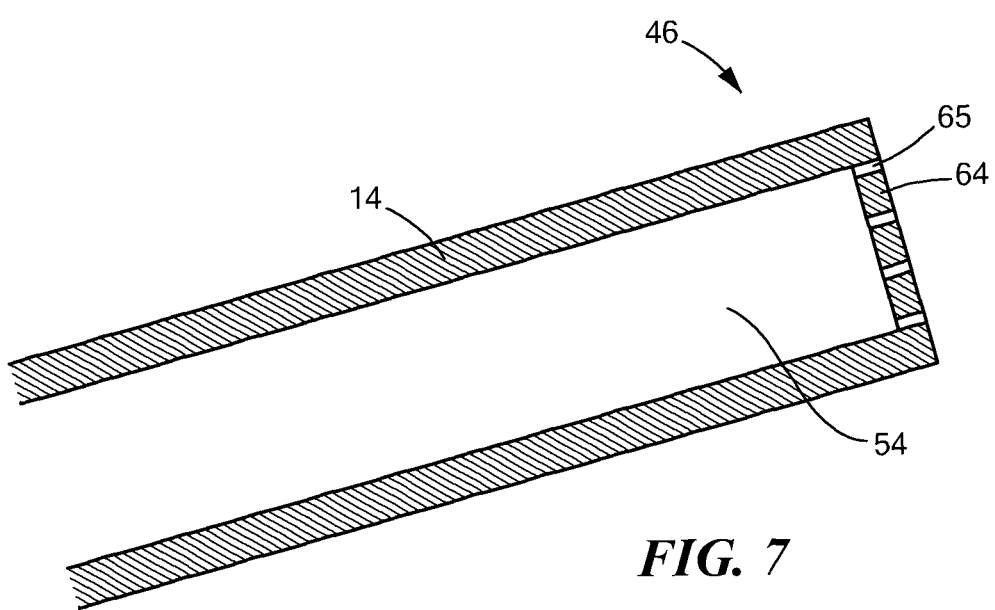
FIG. 7 shows a cross-sectional view of the distal end of an ablation device, the distal tip having a spray nozzle for the application of temperature-sensitizing adjuvant to tissue.

Referring now to FIG. 7, a cross-sectional view of the distal end 46 of an ablation device 14 is shown, the distal end 46 having a spray nozzle 64 for the application of TSA 26 to tissue 10. The spray nozzle 64 includes a plurality of apertures 65 in the distal end 46 of the device 14 through which pressurized TSA 26 may pass and be atomized or broken into small droplets. Each droplet may be, for example, between approximately 0.5 µm and approximately 0.5 mm. The spray nozzle 64 may be in fluid communication with the device lumen 54 and TSA reservoir 40.

Figure 8:
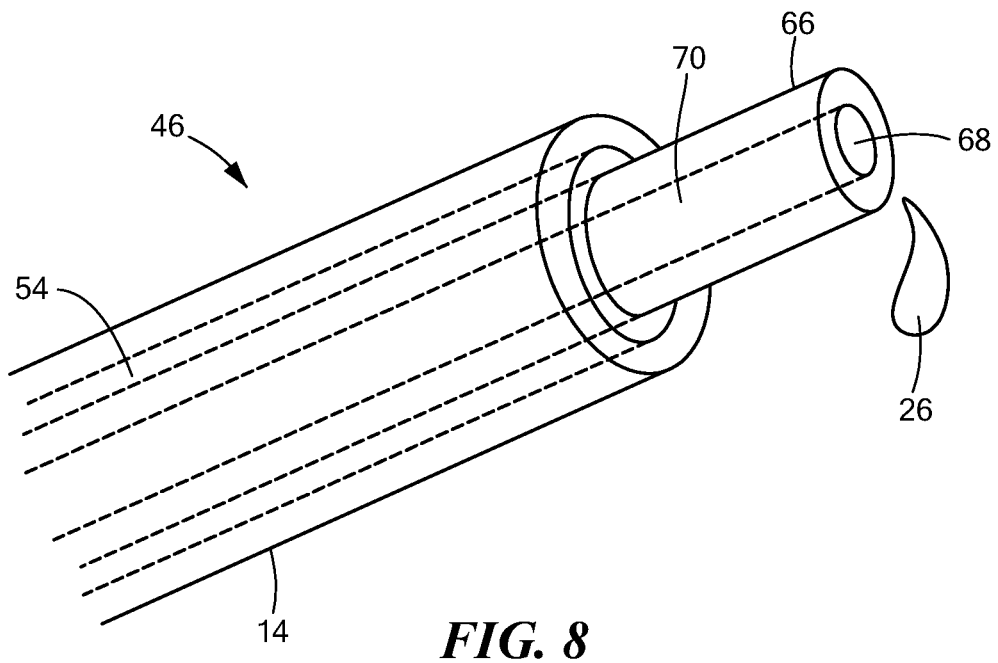
FIG. 8 shows the distal end of an ablation device, the device having a cannula for the application of temperature-sensitizing adjuvant to tissue.
Figure 12:
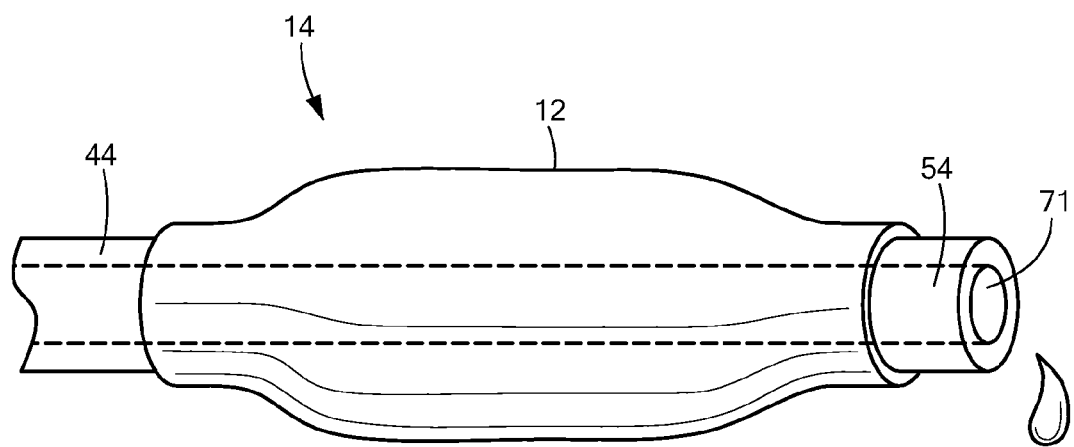
FIG. 12 shows the distal end of an ablation device, the device having a guidewire lumen for the application of temperature-sensitizing adjuvant to tissue.

Referring now to FIG. 8, the distal end 46 of an ablation device 14 is shown, the ablation device 14 having a cannula or other element 66 for the application of TSA 26 to tissue 10. The cannula 66 may be slidably movable within the device lumen 54, and may be advanced beyond the distal end 46 of the device 14 to bring the outlet 68 of the cannula 66 in contact with or near the tissue 10. Temperature-sensitizing adjuvant 26 is then either sprayed (as shown in FIG. 7), dripped (as shown in FIG. 8), or otherwise applied from the outlet 68 to the tissue 10. The cannula 66 may further include a lumen 70, in fluid communication with the outlet 68 and the TSA reservoir 40. Alternatively, the device 14 may be as shown in FIG. 12, wherein the device 14 is an over-the-wire catheter having a guidewire lumen 54 with an outlet 71. Temperature-sensitizing adjuvant 26 is then either dripped, squirted, or otherwise applied from the outlet 71 of the guidewire lumen 54. Further, the device 14 may include an expandable ablation element 12.

Figure 9:
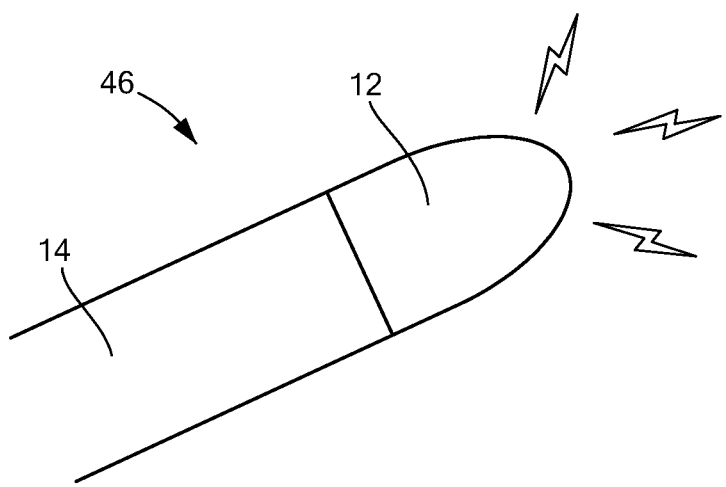
FIG. 9 shows the distal end of an ablation device, the device having an electrode.

Referring now to FIG. 9, the distal end 46 of an ablation device 14 is shown, the distal end 46 including an ablation element 12 (such as an electrode, as shown in FIG. 9). The ablation element 12 may be suited for RF ablation, and is capable of emitting at least low-current energy (for example, 100 mV to approximately 500 mV), and may also be capable of emitting RFA-level energy. The application of low-current energy to target tissue 10 facilitates the creation of a salt-concentration gradient (such as the salt-concentration gradient that develops during slow freezing of tissue) and enhances water permeability of cell membranes. Cells of the tissue 10 respond to an increase in salt concentration by releasing water, resulting in cell dehydration and eventually death. The ablation element 12 may apply low-current energy to the tissue 10 either before, during, or after ablation. Alternatively, the same ablation element 12 may first apply low-current energy to the tissue 10 ("gradient generating mode") and then apply RFA-level energy to the tissue 10 ("ablation mode"). Further, multiple cycles of gradient generating mode/ablation mode may be applied.

Figure 10A:
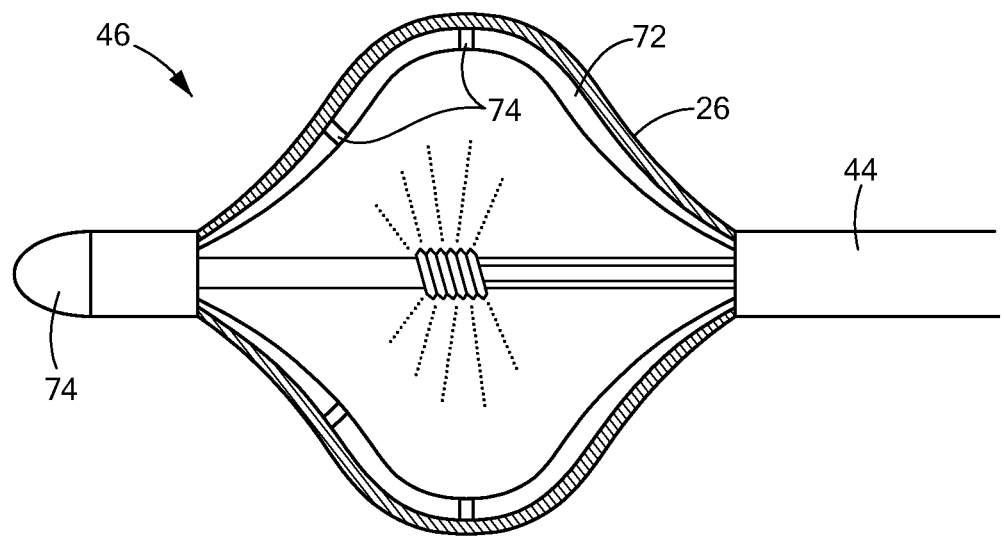
FIG. 10A shows a cross-sectional view of the distal end of an ablation device, the device having both a balloon and one or more electrodes.
Figure 10B:
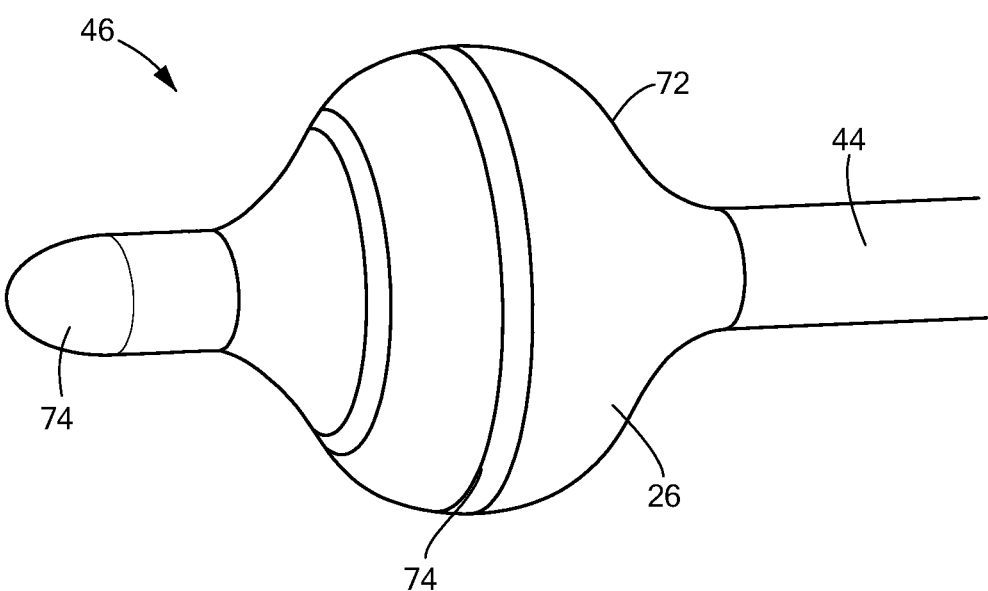
FIG. 10B shows a side view of the distal end of an ablation device, the device having both a balloon and one or more electrodes.

Referring now to FIGS. 10A and 10B, the distal end 46 of an ablation device 14 is shown, the device 14 having more than one treatment elements 12. As shown in FIGS. 10A and 10B, the ablation device 14 includes both a balloon 72 and one or more electrodes 74. The electrodes 74 may be located on the distalmost point of the distal end 46, on the balloon 72, or both. For example, one electrode 74 at the distalmost point of the distal end 46 may be used in gradient generating mode, while other electrodes 74 on the balloon 72 may be used in ablation mode. The one or more electrodes 74 may be in any configuration, for example, discrete electrodes or bands that at least partially circumscribe the balloon 72 (as shown in FIG. 10B). Alternatively, the balloon 72 may be a cryoablation device, with a tip and/or balloon electrodes 74 being used in gradient generating mode. Still further, the balloon 72, electrodes 74, and/or the ablation device 14 may be coated with a layer of TSA 26, as shown and described in FIGS. 4A and 4B.

Figure 11A:
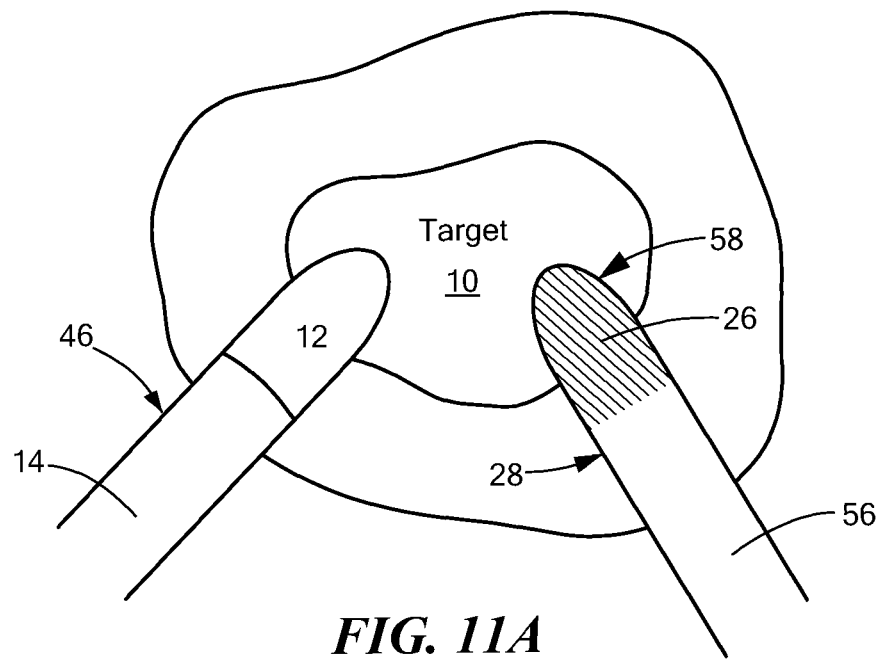
FIG. 11A shows a first exemplary embodiment of an ablation device used in association with a second device for the application of temperature-sensitizing adjuvant to tissue.
Figure 11B:
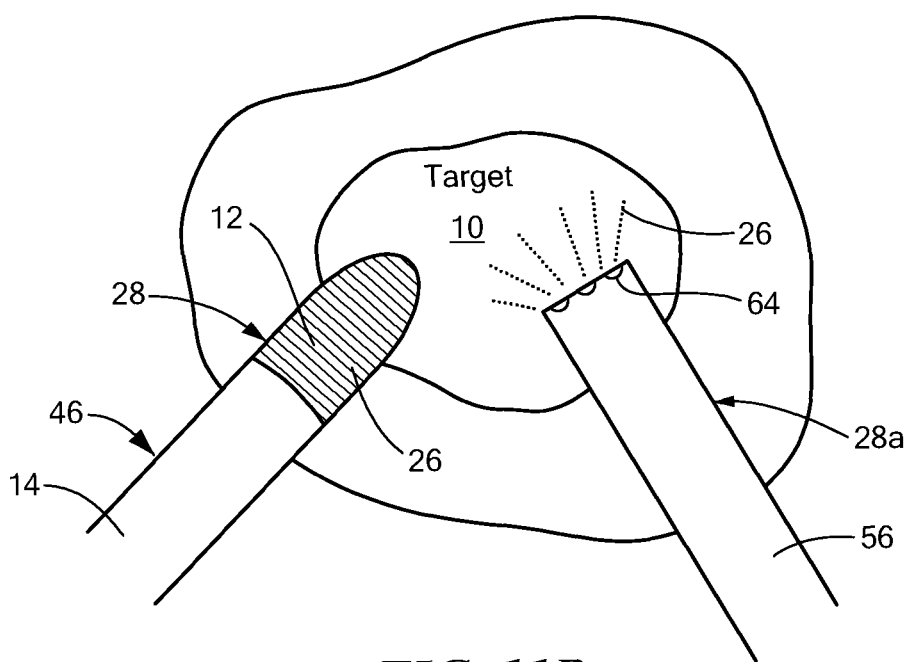
FIG. 11B shows a second exemplary embodiment of an ablation device used in association with a second device for the application of temperature-sensitizing adjuvant to tissue.

Referring now to FIGS. 11A and 11B, a first exemplary embodiment of an ablation device 14 used in association with a second device 56 for the application of TSA to tissue 10 is shown. As shown in FIG. 11A, the ablation device 14 may have a distal end 46 including one or more ablation elements 12. The second device 56 may be any device capable of applying TSA 26 to the target tissue 10. For example, the second device 56 may be a catheter-type device or swab having a distal end 58 coated with a layer of TSA 26 (as shown in FIG. 11A), a device having a spray nozzle (as shown in FIGS. 7 and 11B) or dropper apparatus in fluid communication with a TSA source (such as the TSA reservoir 40), or a hypodermic needle with a syringe containing a volume of TSA 26. As shown in FIG. 11B, both the ablation device 14 and the second device 56 may function as applicators 28, 28a. The ablation device 14 may serve as an applicator 28 when, for example, an ablation balloon or distal end 46 is coated with TSA.

It will be understood that any of the applicators 28 as described herein may be incorporated into either an ablation device 14 or a second device 56. For example, an ablation device 14 may have a spray nozzle 64 at the distalmost end and a balloon ablation element 12. Additionally, any number of second devices 56 may be used. Further, the ablation device 14 may include any number of ablation elements 12, and may be suited for any type of ablation therapy.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of treating tissue to enhance the effects of ablation comprising:
    identifying tissue to receive ablation therapy;
    treating the tissue with a temperature-sensitizing agent; and
    activating an ablation therapy device proximate the treated tissue, the temperature-sensitizing agent being a temperature-sensitizing adjuvant selected from the group consisting of: thermophysical adjuvants, chemotherapeutic adjuvants, vascular adjuvants, immunomodulator adjuvants, and combinations thereof, and the temperature-sensitizing agent being applied to the tissue by an applicator that is integrated with the ablation therapy device, the applicator being an ablation element having an outer surface that is coated with a layer of temperature-sensitizing adjuvant and a layer of temperature-sensitive substrate material between the ablation element and the layer of temperature-sensitizing adjuvant, the layer of substrate material readily separating from the ablation element when substrate material is within a certain temperature range;
    the ablation therapy being at least one of:
        cryoablation and the ablation therapy device is a cryoablation device;
        radiofrequency ablation and the ablation therapy device is a radiofrequency ablation device; and
        combination thereof.

2. The method of claim 1, wherein the ablation element is an expandable element.

3. The method of claim 1, wherein the temperature-sensitizing agent is delivered before or after the application of ablation therapy to the tissue.

4. The method of claim 1, wherein the temperature-sensitizing agent is an electrode.

5. The method of claim 4, wherein the electrode is operable to emit a low current energy of between approximately 100 mV and approximately 500 mV.

6. A method of treating tissue to enhance the effects of ablation comprising:
    identifying tissue to receive ablation therapy;
    treating the tissue with a temperature-sensitizing agent; and
    activating an ablation therapy device proximate the treated tissue, the temperature-sensitizing agent being a temperature-sensitizing adjuvant selected from the group consisting of: thermophysical adjuvants, chemotherapeutic adjuvants, vascular adjuvants, immunomodulator adjuvants, and combinations thereof, and the temperature-sensitizing agent being applied to the tissue by an applicator that is integrated with the ablation therapy device, the applicator being a distal end of the ablation therapy device, the distal end being coated with a layer of temperature-sensitizing adjuvant and having a layer of temperature-sensitive substrate material between the ablation element and the layer of temperature-sensitizing adjuvant, the layer of substrate material readily separating from the ablation element when substrate material is within a certain temperature range;
    the ablation therapy being at least one of:
        cryoablation and the ablation therapy device is a cryoablation device;
        radiofrequency ablation and the ablation therapy device is a radiofrequency ablation device; and
        combination thereof.

7. The method of claim 6, wherein the distal end of the device includes a plurality of indentations each sized to contain a volume of temperature-sensitizing adjuvant.

8. The method of claim 6, wherein the ablation element is an expandable element.

9. The method of claim 6, wherein the temperature-sensitizing agent is delivered before or after the application of ablation therapy to the tissue.

10. The method of claim 6, wherein the temperature-sensitizing agent is an electrode.

11. The method of claim 10, wherein the electrode is operable to emit a low current energy of between approximately 100 mV and approximately 500 mV.

* * * * *